United States Patent [19]

Frazee, Jr. et al.

[11] 4,027,977

[45] June 7, 1977

[54] METHOD AND APPARATUS FOR DETERMINING RATIO OF CORE RADIUS TO CLADDING RADIUS IN CLAD OPTICAL FIBERS

[75] Inventors: Ralph Edward Frazee, Jr., Spotswood Borough; Laurence Shrapnell Watkins, Hopewell Township, Mercer County, both of N.J.

[73] Assignee: Western Electric Company, New York, N.Y.

[22] Filed: Dec. 17, 1975

[21] Appl. No.: 641,697

[52] U.S. Cl. .............................. 356/111; 250/550; 356/159
[51] Int. Cl.² ................... G01B 9/02; G01B 11/08; G01B 11/12
[58] Field of Search ... 356/159, 161, 199, 106–108, 356/111; 250/559–560, 571, 550; 65/29; 307/235 A, 235 J; 328/115, 150

[56] References Cited

UNITED STATES PATENTS

| | | | |
|---|---|---|---|
| 3,659,950 | 5/1972 | Troll et al. | 356/199 |
| 3,709,610 | 1/1973 | Kruegle | 356/111 |
| 3,797,939 | 3/1974 | Pryor | 356/111 |
| 3,879,128 | 4/1975 | Presby | 250/571 |
| 3,925,733 | 12/1975 | Moore | 328/114 |
| 3,982,816 | 9/1976 | Watkins | 356/111 |

OTHER PUBLICATIONS

Watkins, L. S., "Scattering from Side-Illuminated Clad Glass Fibers for Determination of Fiber Parameters", Jr. of Optical Soc. of America, vol. 64, 6-1974, pp. 767-772.

Primary Examiner—John K. Corbin
Assistant Examiner—Wm. H. Punter
Attorney, Agent, or Firm—G. D. Green; D. J. Kirk

[57] ABSTRACT

Method and apparatus are disclosed for determining a parameter of a clad optical fiber from the scattering angle at the maximum of a modulation component in a forward far-field scattering pattern produced by directing a monochromatic coherent light beam at the fiber. One such parameter is the ratio between core radius and cladding radius.

4 Claims, 5 Drawing Figures

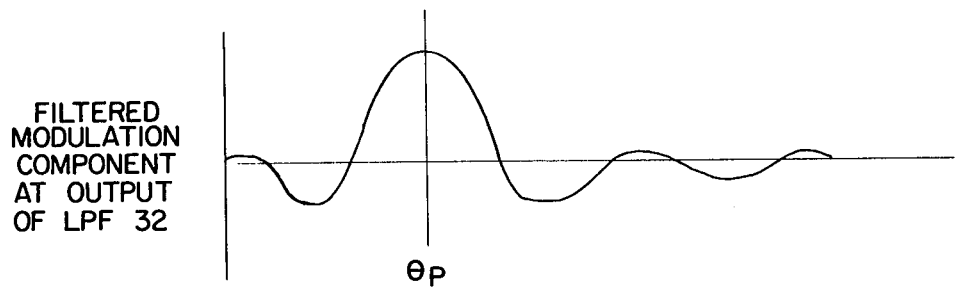
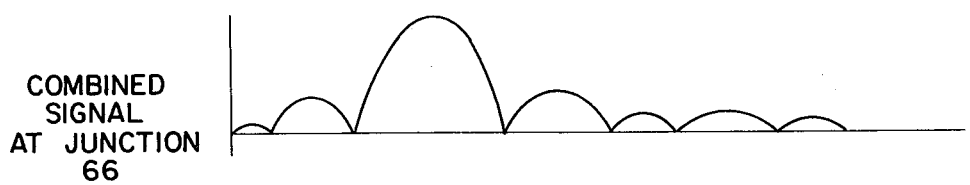
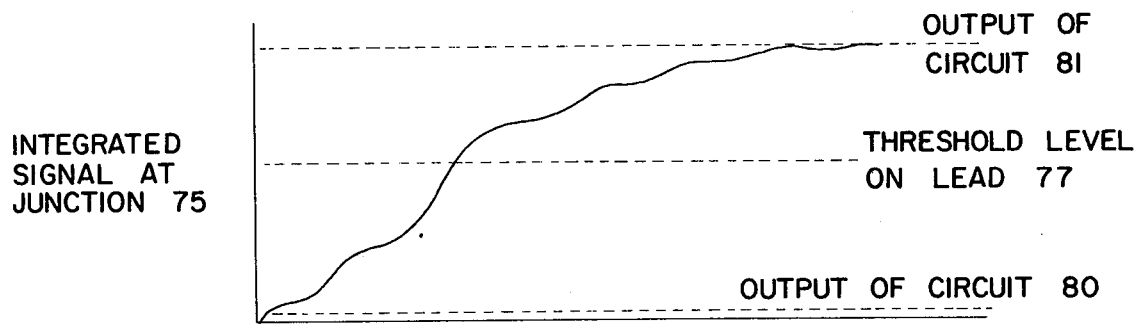
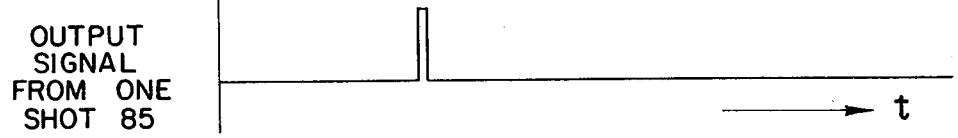
FIG. 5

4,027,977

METHOD AND APPARATUS FOR DETERMINING RATIO OF CORE RADIUS TO CLADDING RADIUS IN CLAD OPTICAL FIBERS

BACKGROUND OF THE INVENTION

1. Field of the Invention

This invention relates to measuring optical fibers, and more particularly, to determining the ratio of core radius to cladding radius in a clad optical fiber.

2. Description of the Prior Art

It is known to measure various parameters of an optical fiber by directing a coherent light beam such as a laser beam at the fiber and analyzing the far-field forward scattering pattern thus produced. The outer radius of such a fiber can be determined by counting the number of fringes in a particular region of the scattering pattern. For a clad fiber, the ratio of core radius to cladding radius can be determined by measuring the position of an angle in the scattering pattern where modulation of the fringes starts, thus enabling the core radius to be found from the outer cladding radius. These methods depend on knowing the refractive index of an unclad fiber, or of the cladding of a clad fiber. Such measuring methods are disclosed in a copending application of L. S. Watkins, Ser. No. 482,707, filed June 21, 1974, issued as U.S. Pat. No. 3,982,816 on Sept. 28, 1976, which is assigned to this assignee. Methods and apparatus useful for detecting fringes in a scattering pattern are disclosed in copending application Ser. No. 634,717, filed Nov. 24, 1975 of L. S. Watkins, which is also assigned to this assignee.

Given that the ratio of core radius to cladding radius can be determined from the angle in the forward scattering pattern at which fringe modulation begins, it is desirable to provide a method and apparatus for automatically determining this angle.

SUMMARY OF THE INVENTION

The invention comprises a method of determining a parameter of an optical fiber having a core and a cladding. A coherent monochromatic light beam is directed at the fiber to generate a far-field scattering pattern including contributions from portions of the beam reflected by the fiber, portions of the beam refracted by both the core and the cladding of the fiber, and portions of the beam refracted only by the cladding of the fiber. The scattering angle in the scattering pattern at which the maximum of a fringe modulation component occurs is detected, and converted into the parameter. One such parameter is the ratio between core radius and cladding radius.

Apparatus for performing the method of the invention is also disclosed.

These and other aspects of the invention will be apparent from the attached drawings and the following description.

BRIEF DESCRIPTION OF THE DRAWINGS

FIG. 5 is a series of graphs representing electrical signals in the peak detector of FIG. 4.

DETAILED DESCRIPTION

Figure 1:
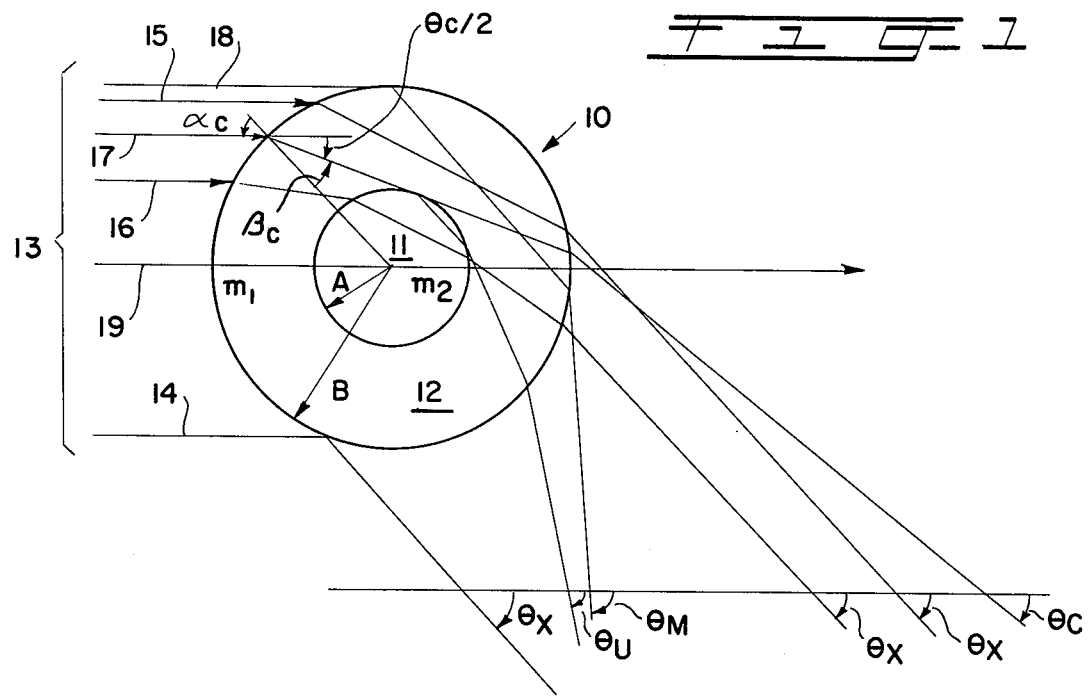
FIG. 1 is a diagram of a clad optical fiber showing the effect of the fiber on rays of an incident light beam.

FIG. 1 is a ray-trace diagram showing an end-on view of a clad optical fiber and rays from a beam of monochromatic coherent light being scattered by the fiber. This diagram is useful in demonstrating how a scattering angle $\theta_c$, where modulation begins in a forward far-field scattering pattern, is related to the ratio of core radius to cladding radius.

Referring to FIG. 1, fiber 10 comprises core 11 having radius A and refractive index $m_2$, and cladding 12 having outer radius B and refractive index $m_1$. An incident beam 13 of monochromatic coherent light, such as a laser beam, is directed at fiber 10. In FIG. 1, various light rays from beam 13 are shown as they are affected by fiber 10.

Rays from beam 13 are diffracted, reflected, or refracted by fiber 10 to diverge from the centerline of beam 13 at various scattering angles. Diffracted rays are not of interest for the purposes of the invention. Rays that are reflected by fiber 10 occur in a first scattering angle range, rays refracted by only cladding 12 occur in a second scattering angle range, and rays refracted by both cladding 12 and core 11 occur in a third scattering angle range. These ranges overlap, thus rays of each type can be scattered at the same angle. This principle is illustrated with rays 14, 15, and 16.

Ray 14 is reflected from the outer surface of fiber 10 and proceeds at a scattering angle $\theta_x$ with respect to the incident beam. Ray 15 is refracted by cladding 12, also at scattering angle $\theta_x$. Ray 16 is refracted by cladding 12, core 11, then again by cladding 12, and is also scattered at angle $\theta_x$. Thus, it can be seen that rays 14, 15, 16, which are each affected differently by fiber 10, are each scattered at the same angle $\theta_x$.

Rays 17, 18, and 19 have been chosen to show the limits of the second and third ranges. Ray 17 grazes the edge of core 11. If ray 17 is moved to barely miss core 11, it will be scattered at an angle $\theta_c$. However, if ray 17 is moved to barely pass through a portion of core 11, it will be scattered at angle $\theta_u$. It can be seen that ray 18, which just grazes cladding 12, is refracted to proceed at the maximum scattering angle $\theta_m$, and that ray 19, which passes through the axis of the fiber, proceeds at a scattering angle of 0°.

The second range of scattering angles through which rays refracted only by cladding 12 pass is from $\theta_c$ to $\theta_m$, and the third range of scattering angles through which rays refracted by both core 11 and cladding 12 pass is from 0° to $\theta_u$. Thus, between $\theta_c$ and $\theta_u$, these ranges overlap, and both kinds of refracted rays exist; those refracted by only cladding 12, and those refracted by both core 11 and cladding 12. The first range of scattering angles of reflected rays extends from 0° to above $\theta_m$.

Rays leaving fiber 10 at the same scattering angle interfere in the far field at a distance that is large with respect to the diameter of fiber 10. Interference in the far field among rays having the same scattering angle, such as among reflected ray 14, and refracted rays 16 and 17, causes fringes in the scattering pattern. These fringes can be counted to determine the outer diameter of the fiber, as is noted above. Interference between the two kinds of refracted rays causes modulation of the fringes in the portion of the scattering pattern between $\theta_c$ and $\theta_u$. Fringes also exist below $\theta_c$ because of interference between reflected rays and rays such as ray 19 refracted by both the cladding and the core, and above $\theta_u$ because of interference between reflected rays and rays such as ray 18 refracted only by the cladding.

Figure 2:
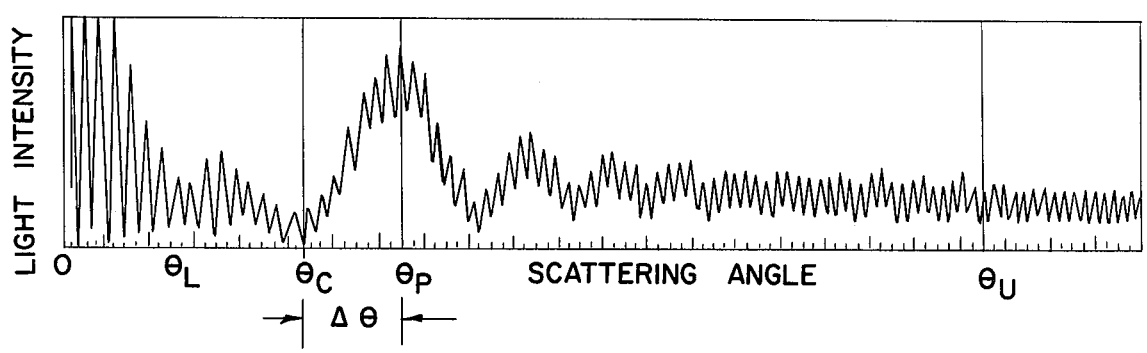
FIG. 2 is a graph of a far-field scattering pattern for a clad optical fiber.

FIG. 2 is a graphical representation of the intensity of light in the far-field scattering pattern from a clad optical fiber such as fiber 10. In FIG. 2, the horizontal axis represents the scattering angle in degrees and the vertical axis represents light intensity in arbitrary units. Between scattering angles of 0° and about 7°, light diffracted by fiber 10 is dominant. As noted above, diffracted light is not utilized in the measuring techniques under discussion. Above about 7°, reflected light and refracted light are dominant. Angles $\theta_c$ and $\theta_u$ are marked in FIG. 2, and it can be seen that the fringes in the scattering pattern are modulated between these angles, with the magnitude of the modulation component rising to a maximum near $\theta_c$.

A relationship between scattering angle $\theta_c$ and the ratio A/B between core diameter and cladding diameter will now be developed. Referring again to FIG. 1, incidence angle $\alpha_c$ is the angle of incidence of ray 17 and $\beta_c$ is the angle between ray 17 and the normal to the surface of cladding 12. Since ray 17 meets core 11 tangentially, $$A/B = \sin \beta_c. \tag{1}$$

From Snell's law $$\sin \beta_c = \sin \alpha_c / m_1. \tag{2}$$

Since $$\beta_c = \alpha_c - \theta_c/2 \tag{3}$$

from equations (2) and (3) we can derive $$\tan \alpha_c = m_1 \sin (\theta_c/2) / [m \cos (\theta_c/2) - 1] \tag{4}$$

and $$\sin \alpha_c = m_1 \sin (\theta_c/2) / \sqrt{m_1^2 + 1 - 2m_1\cos(\theta_c/2)}. \tag{5}$$

Thus, from equations (1), (2), and (5)

$$A/B = \sin (\theta_c/2) / \sqrt{m_1^2 + 1 - 2m_1\cos (\theta_c/2)}. \tag{6}$$

Equation (6) can be used with a measured value of $\theta_c$ and a known value of refractive index $m_1$ to determine ratio A/B. If the cladding radius B is known, then the core radius A can be determined.

It is not practical to measure $\theta_c$ directly, but we have discovered that a measurement having sufficient accuracy can be obtained from a scattering pattern such as that shown in FIG. 2 by measuring the angular position of the maximum of the fringe modulation component, an angle we have labeled $\theta_p$ in FIG. 2. Angle $\theta_p$ is offset slightly from $\theta_c$, but this offset tends to be substantially constant over a fairly wide range, and little error is introduced by introducing a constant $\Delta\theta$ that can be used with measured values of $\theta_p$ to determine the ratio A/B. For use with $\theta_p$ and $\Delta\theta$, equation (6) becomes $$A/B = \sin [(\theta_p - \Delta\theta)/2] / \sqrt{m_1^2 + 1 - 2m_1\cos[(\theta_p - \Delta\theta)/2]}. \tag{7}$$

It is thus necessary to provide means for detecting the first modulation maximum in the scattering pattern from the fiber being measured. This can be accomplished, for example, by the apparatus shown in FIG. 3.

Figure 3:
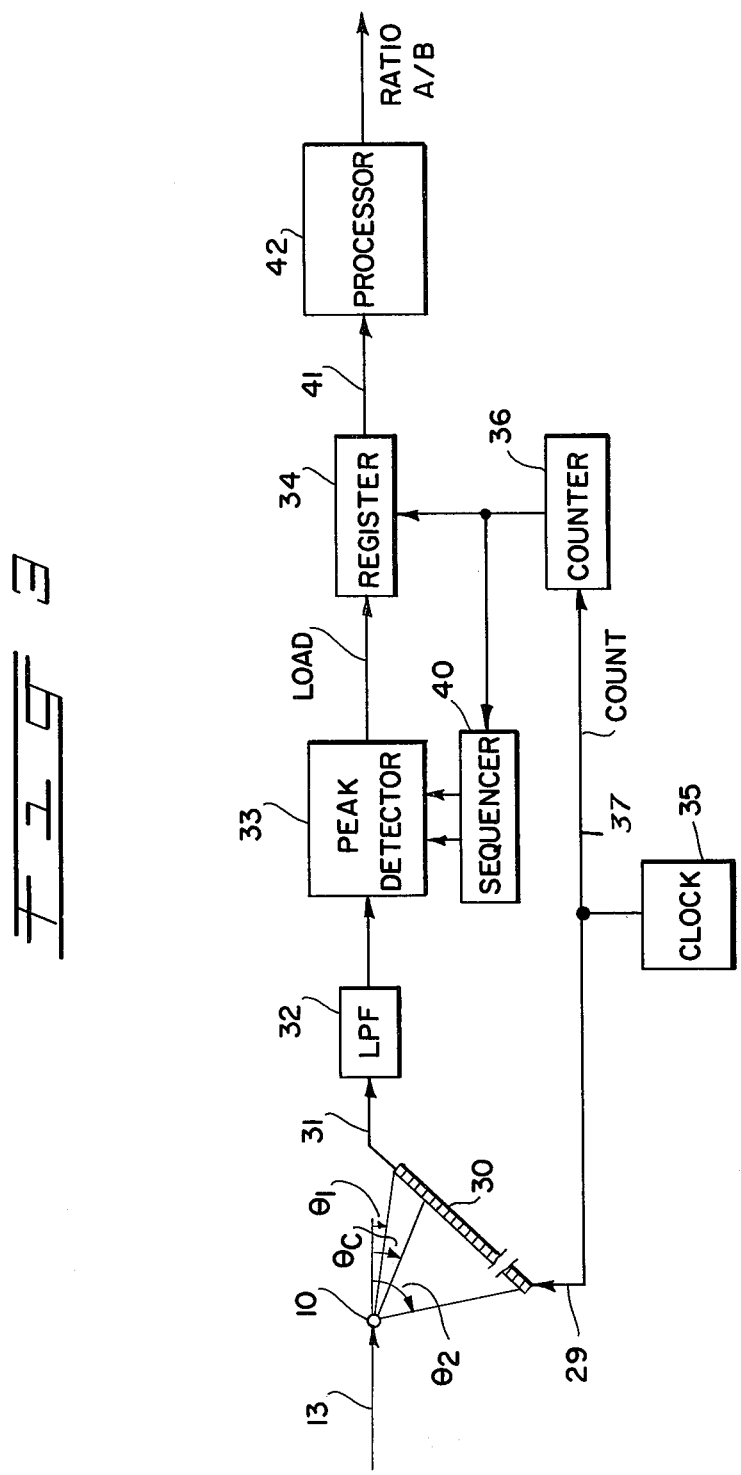
FIG. 3 is a partially diagrammatic, partially schematic diagram of apparatus according to the invention for determining the ratio of core diameter to fiber diameter.

Referring to FIG. 3, laser beam 13 is shown directed onto clad fiber 10. The far-field scattering pattern thus produced falls on linear diode array 30, which comprises a number of diodes, for example, 512. Such a diode array can be self scanning, that is, the array can include circuitry to sequentially connect each diode to output line 31 in response to clock pulses applied on input lead 29. Thus, a time-varying signal can be generated on lead 31 which represents the scattering pattern. Such self-scanning diode arrays are well known in the art, for example, the 7000 series self-scanning photodiode arrays supplied by Integrated Photomation, Ltd., Dorchester, England. Diode array 30 can be positioned in the far-field scattering pattern to sense just the region where the modulation peak is expected to occur, or a larger region, such as from angle $\theta_1$ to $\theta_2$, which encompasses enough fringes of the scattering pattern for determining the outer diameter of the fiber as described in the copending L. S. Watkins applications noted above.

The time-varying analog signal on line 31 is filtered by low-pass filter (LPF) 32 to remove the fringe information and leave essentially the modulation component. The output signal from LPF 32 is graphically represented in FIG. 5. The filtered signal from LPF 32 is then passed through peak detector 33, which provides an output pulse to the LOAD input of register 34 when the modulation signal from LPF 32 reaches a peak. An exemplary embodiment of a peak detector suitable for this purpose will be described below.

Clock 35 generates a train of pulses to drive diode array 30 via line 29 and counter 36 via line 37. The pulse rate can be, for example, 1 megacycle. Counter 36 can be chosen to have the same number of counts as diode array 30 has diodes, so that the count in counter 36 always corresponds to the number of the diode being scanned. An alternative arrangement can be to supply counter 36 with pulses at a different rate from those supplied to diode array 30, and to reset counter 36 at the beginning of every scan of diode array 30. Circuitry for such an arrangement would be readily apparent to one skilled in the art.

Counter 36 is connected to register 34 so that the count in counter 36 is loaded into register 34 when a pulse appears at the LOAD input of register 34 from peak detector 33. Since counter 36 counts periodic pulses, the magnitude of the count stored in register 34 is proportional to the time from the beginning of the scan of diode array 30, and also the magnitude of $\theta_p$. The magnitude of $\theta_p$ can be calculated by multiplying the count in register 34 by an appropriate constant of proportionality.

Sequencer 40, which is connected to the output of counter 36, provides timing pulses at appropriate points in the scanning cycle to drive peak detector 33, as will become apparent below in the description of the exemplary embodiment of peak detector 33.

Signals representing the contents of register 34 are directed to processor 42, which converts the magnitude of $\theta_p$ stored in register 34 into the ratio A/B according to a mathematical relationship, such as equation (7). Processor 42 can be an analog device or a digital device, as is convenient, and signals can be directed to and taken from processor 42 in analog or digital form as desired. Processor 42 may be a digital computer programmed to calculate ratio A/B from $\theta_p$, as well as other quantities. For example, processor 42 could also calculate the core radius from a known or calculated value of cladding radius. The provision of suitable means for processor 42 is well within the capabilities of those skilled in the art.

Figure 4:
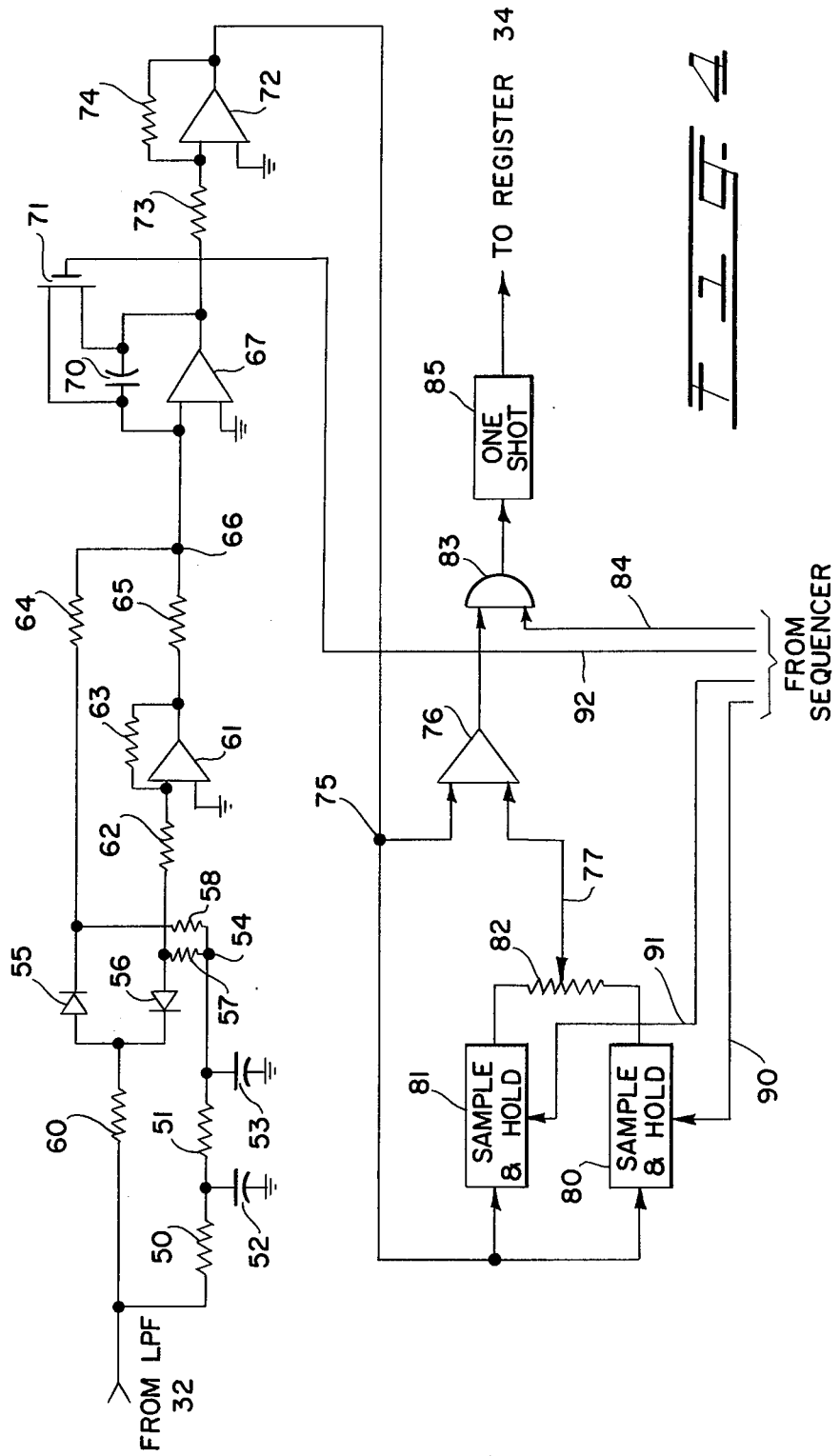
FIG. 4 is a more detailed schematic diagram of an embodiment of a peak detector for the apparatus shown in FIG. 3.

FIG. 4 shows an exemplary embodiment of a peak detector that can be used for peak detector 33. FIG. 5 shows graphical representations of signals in the peak detector of FIG. 4.

Referring to FIG. 4, the filtered modulation signal from LPF 32 is applied to an averaging circuit comprising resistors 50 and 51 and capacitors 52 and 53. The voltage at junction 54, which corresponds to the average level of the filtered modulation signal, biases diodes 55 and 56 at this average level through resistors 57 and 58, respectively. The filtered modulation signal is connected through resistor 60 to the anode of diode 55 and the cathode of diode 56. When the filtered modulation signal is greater than the voltage at junction 54, diode 55 conducts and diode 56 blocks, and when the filtered modulation signal is less than the voltage at junction 54, diode 56 conducts and diode 55 blocks. Thus, diodes 55 and 56 act as switches.

The output from diode 56 is connected to an inverter comprising operational amplifier 61 and resistors 62 and 63, which changes the polarity of excursions of the filtered modulation signal below the level of the voltage at junction 54. Resistors 64 and 65 combine signals from diode 55 and amplifier 61 to produce a signal at junction 66 that is essentially a rectified version of the filtered modulation signal.

Operational amplifier 67 and capacitor 70 form an integrator that integrates the signal at junction 66 over the time for one scan of the scattering pattern. Field-effect transistor 70 discharges capacitor 70 at the end of each scan to reset the integrator. An inverter comprising operational amplifier 72 and resistors 73 and 74 inverts the output of the integrator. The combined signal at junction 66 and the integrated signal at junction 75 are represented in FIG. 5.

Comparator 76 compares the signal at junction 75 with a reference signal on lead 77 generated by the combination of sample-and-hold circuits 80 and 81 and potentiometer 82. When the signal at junction 75 is greater than that on line 77, the output of comparator 76 is a logical 1; when the signal at junction 75 is less than that on line 77, the output of comparator 76 is a logical 0.

AND-gate 83 receives the logical signal from comparator 76 and an enabling signal from sequencer 40 via line 84. When both these signals are 1, output of gate 83 is 1. A 0-1 transition in the output of gate 83 causes one-shot circuit 85 to generate a single pulse to load register 34 (FIG. 3). The 0-1 transition in the output of comparator 76 that fires one-shot 85 occurs when the signal at junction 75 becomes greater than the threshold level on lead 77. A representation of the output signal from one-shot 85 is shown in FIG. 5.

Sample-and-hold circuits 80 and 81 are connected to junction 75 and to enabling leads 90 and 91, respectively, from sequencer 40. At the beginning of each scan cycle, sequencer 40 generates a pulse on lead 92 to discharge capacitor 70, and then a pulse on lead 90 to cause circuit 80 to sample and hold the signal at junction 75. At the end of each scan cycle, sequencer 40 generates a pulse on lead 91 to cause circuit 81 to sample and hold the signal at junction 75. Thus, the signal levels at the beginning and end of a scan cycle are held for the next cycle. A threshold level between the beginning and ending levels is obtained on lead 77 by means of potentiometer 77. This threshold level is set at about the level of the point of maximum slope of the signal at junction 75. In FIG. 5, the outputs of circuits 80 and 81 and the threshold level on lead 77 are represented by dotted lines. As can be seen from FIG. 5, the point of maximum slope corresponds to the modulation peak at angle $\theta_p$. Amplitude changes in the modulation signal, which can result from variations in either the transmission characteristics or the position of optical fiber 10, thus cause circuits 80 and 81 to correspondingly change the threshold level on line 77 so that the point in time when the integrated signal reaches the threshold level substantially tracks the point in time of the peak of the modulation signal.

Sequencer 40 places logical 1 on lead 84 to enable gate 83 during the interval when the peak in the modulation signal is expected to occur, and logical 0 to disable gate 83 to block spurious signals from gate 83 that could affect regsiter 34 during intervals when capacitor 71 is being discharged or when circuits 80 and 81 are being operated.

Sequencer 40 can comprise a series of decoders that respond to different states of counter 36 to provide signals on lines 84, 90, 91, and 92. For example, if diode array 30 comprises 512 diodes and counter 36 counts from 0 to 511, sequencer 40 can be arranged to generate a pulse on lead 92 at count 0, a pulse on lead 90 at count 1, an enabling level on lead 84 from counts 2 to 510, and a pulse on lead 91 at count 511. Another sequencer embodiment could comprise a series of delay and pulse circuits arranged to generate pulses at appropriate times. Circuit arrangements for such an embodiment would be apparent to those skilled in the art.

One skilled in the art may make changes and modifications to the embodiments of the invention disclosed herein, and may devise other embodiments, without departing from the spirit and the scope of the invention.

What is claimed is:

1. A method of determining the ratio of the core radius to the cladding radius, A/B, of a clad optical fiber which comprises:
   directing a monochromatic coherent light beam at the fiber to generate a far-field scattering pattern including contributions from portions of the beam reflected by the fiber, portions of the beam refracted by both the core and the cladding of the fiber, and portions of the beam refracted only by the cladding of the fiber;
   detecting a scattering angle, $\theta_p$, at which the maximum of a fringe modulation component occurs in the scattering pattern; and
   converting the detected scattering angle, $\theta_p$, into the ratio A/B from the relationship:

$$A/B = \sin\left[(\theta_p - \Delta\theta)/2\right] / \sqrt{m_1^2 + 1 - 2m_1\cos\left[(\theta_p - \Delta\theta)/2\right]}$$

where $\Delta\theta$ is a constant that is substantially the difference between $\theta_p$ and the angle $\theta_c$ where modulation begins, and $m_1$ is the refractive index of the cladding.

2. The method of claim 1 wherein the detecting step comprises:

converting the scattering pattern into a time-varying electrical signal;

filtering the time-varying signal to isolate the modulation component; and timing the interval from the start of the time-varying signal to the maximum of the modulation component, the length of the interval being proportional to the angle $\theta_p$.

3. Apparatus for determining the ratio of the core radius to the cladding radius, A/B, of a clad optical fiber, which comprises:

a source of monochromatic, coherent light directed at the fiber to produce a far-field scattering pattern including contributions from portions of the beam reflected by the fiber, portions of the beam refracted by both the core and the cladding of the fiber, and portions of the beam refracted only by the cladding of the fiber;

means for detecting a scattering angle, $\theta_p$, at which the maximum of a fringe modulation component occurs in the scattering pattern; and means for converting the detected scattering angle, $\theta_p$, into the ratio A/B from the relationship:

$$A/B = \sin[(\theta_p - \Delta\theta)/2]/\sqrt{m_1^2 + 1 - 2m_1\cos[(\theta_p - \Delta\theta)/2]}$$

where $\Delta\theta$ is a constant that is substantially the difference between $\theta_p$ and the angle $\theta_c$ where modulation begins, and $m_1$ is the refractive index of the cladding.

4. The apparatus of claim 3 wherein the means for detecting comprises:

means for converting the scattering pattern into a time-varying electrical signal;

a filter connected to the converting means for isolating the modulation component of the time-varying signal; and means for timing the interval from the start of the time-varying signal to the peak of the modulation component, the length of the interval being proportional to the angle $\theta_p$.

* * * * *